US00PP24680P3

(12) United States Plant Patent
Deng et al.

(10) Patent No.: US PP24,680 P3
(45) Date of Patent: Jul. 22, 2014

(54) *CALADIUM* PLANT NAMED 'UF 44-4'

(50) Latin Name: *Caladium×hortulanum*
Varietal Denomination: UF 44-4

(75) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 158 days.

(21) Appl. No.: 13/573,133

(22) Filed: Aug. 24, 2012

(65) Prior Publication Data

US 2012/0324610 P1 Dec. 20, 2012

(51) Int. Cl.
*A01H 5/00* (2006.01)

(52) U.S. Cl.
USPC ..... Plt./373

(58) Field of Classification Search
USPC ..... Plt./373
See application file for complete search history.

(56) References Cited

PUBLICATIONS

Deng, Z. et al. "UF 44-4; a dwarf red lance-leaved *caladium* cultivar" Hortscience 46.7 pp. 1049-1051 ASHS Jul. 2011.*

* cited by examiner

*Primary Examiner* — Wendy C Haas
(74) *Attorney, Agent, or Firm* — Jondle Plant Sciences Division of Swanson & Bratschun, L.L.C.

(57) ABSTRACT

A new and distinct cultivar of *caladium* plant named 'UF 44-4', characterized by its compact growth habit, plants with numerous lance-type leaves that are slightly undulate, leaves that have bright red center and green margins, and plants that are attractive in containers or landscapes.

4 Drawing Sheets

ACKNOWLEDGMENT OF FEDERAL RESEARCH SUPPORT

This invention was made with government support under FLA-BRA-04162 awarded by the Cooperative State Research, Education, and Extension Service, USDA. The government has certain rights in the invention.

Genus and species: *Caladium×hortulanum.*
Variety denomination: 'UF 44-4'.

BACKGROUND OF THE NEW PLANT

The present invention relates to a new and distinct cultivar of *caladium* plant, botanically known as *Caladium×hortulanum,* commercially referred to as a strap leaf-type or lance leaf-type and hereinafter referred to by the name 'UF 44-4'.

*Caladiums* are ornamental aroids frequently used as pot and landscape plants for their colorful foliage and ease of growing. The objective of the Inventors' breeding program is to create new *caladium* cultivars that have compact growth habit, numerous leaves, attractive foliage, and exceptional container and landscape performance.

'UF 44-4' originated from selfing the *caladium* plant 'S79-206' in June of 2000 in Bradenton, Fla. 'S79-206' was a selection of 'Florida Sweetheart' (U.S. Plant Pat. No. 8,526). The new *caladium* 'UF 44-4' was discovered and selected by the inventors as a single plant in September of 2001. 'UF 44-4' has been found to retain its distinctive characteristics through at least 10 generations of successive asexual propagations via tuber divisions since March of 2002.

Plant Breeder's Rights for this cultivar have not been applied for. 'UF 44-4' has not been made publicly available more than one year prior to the filing of this application.

SUMMARY OF THE INVENTION

The following are the most outstanding and distinguishing characteristics of this new variety when grown under (normal or standard) horticultural practices in Wimauma, Fla. These characteristics distinguish 'UF 44-4' as a new and distinct cultivar of *caladium:*

1. Compact plant habit;
2. Numerous lance or strap-type leaves that are slightly undulate and have a bright red center and green margins; and
3. Attractive plants in containers or landscapes.

DESCRIPTION OF THE PHOTOGRAPHS

The accompanying photographs illustrate the overall appearance of the new *caladium.* These photographs show the colors as true as can be reasonably obtained in colored reproductions of this type. Colors in the photographs may differ slightly from the color values cited in the detailed botanical description, which accurately describe the colors of the new *caladium.*

DESCRIPTION OF THE NEW VARIETY

Figure 1:
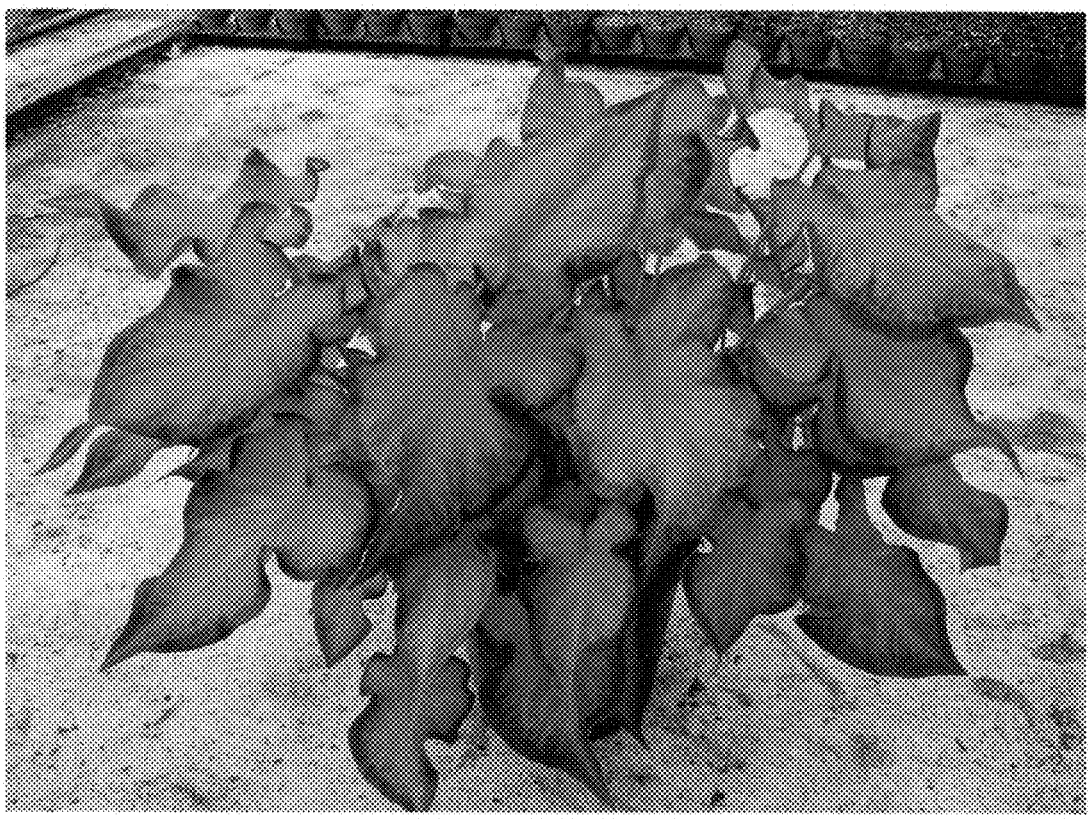
FIG. 1 is a side view of the new variety 'UF 44-4' grown in a 20-cm diameter container in a shadehouse.
Figure 2:
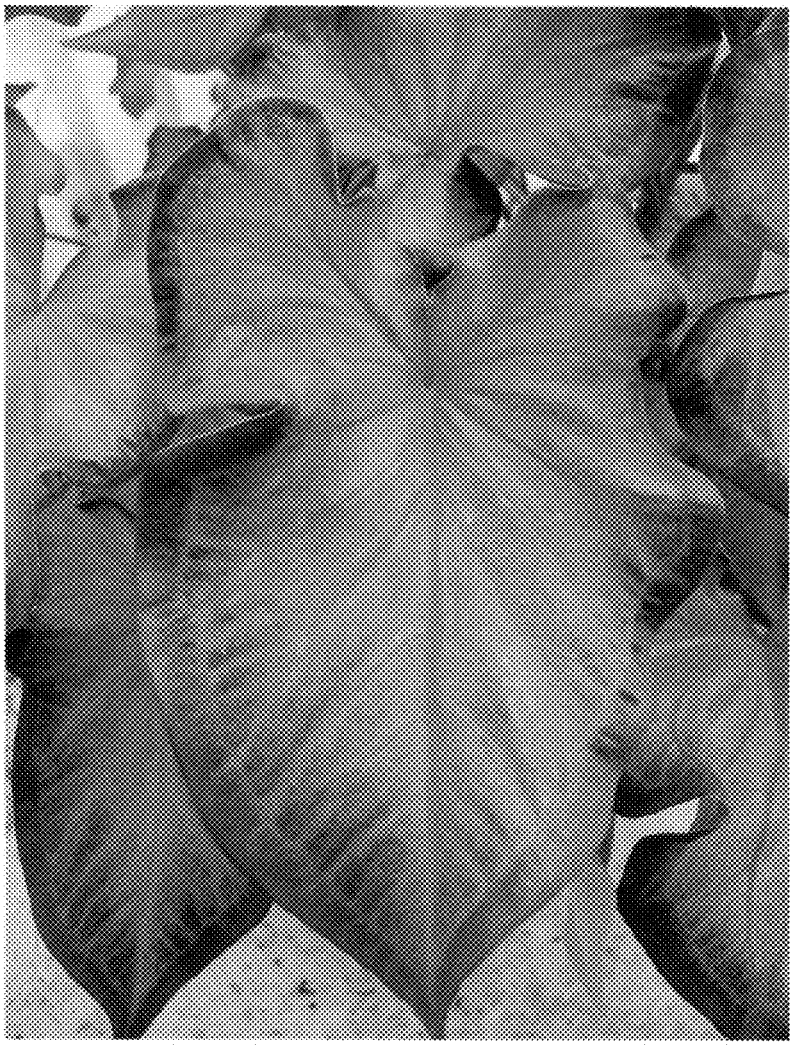
FIG. 2 is a top view of a typical leaf of the new variety 'UF 44-4' grown in a 20-cm diameter container in a shadehouse.
Figure 3:
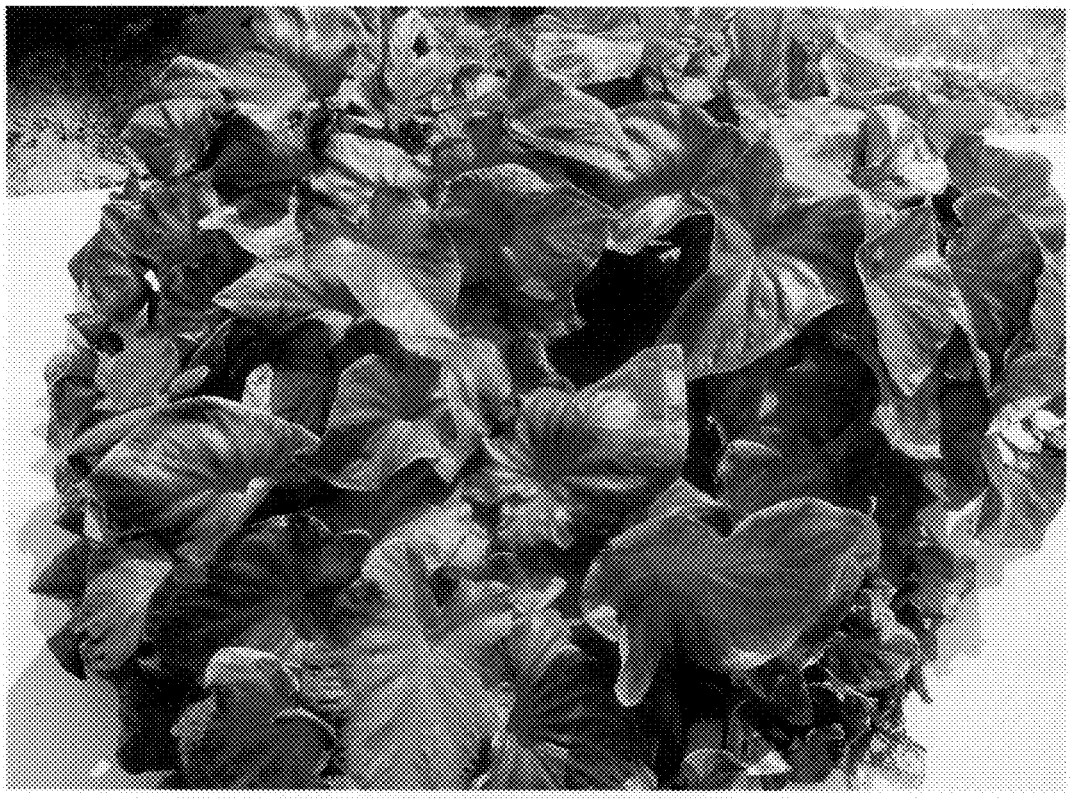
FIG. 3 is a top view of typical plants of the new variety 'UF 44-4' grown in an outdoor nursery.
Figure 4:
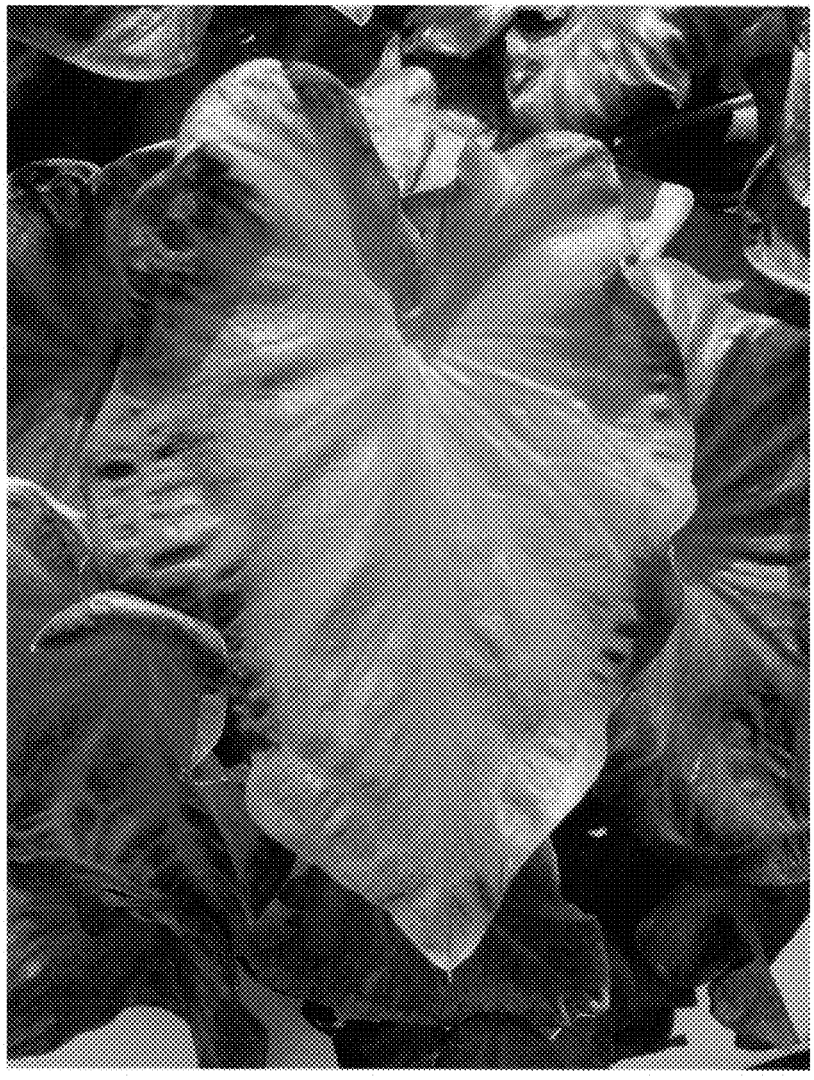
FIG. 4 is a top view of a typical leaf of the new variety 'UF 44-4' grown in an outdoor nursery.

In the following description, color references are made to The Royal Horticultural Society Colour Chart, 1986 Edition, except where general terms of ordinary dictionary significance are used.

The following observations and measurements describe plants grown in 20-cm containers in Wimauma, Fla. during the summer in a polypropylene-covered shadehouse and plants grown in ground beds in Wimauma, Fla. during the late summer in an outdoor nursery. All plants were grown under conditions and practices similar to those generally used in commercial *caladium* production.

During the production of the plants, day temperatures ranged from approximately 23.5° C. to 34.4° C., night temperatures ranged from approximately 20.5° C. to 23.5° C., and light levels were approximately 944 foot-candles in the shadehouse and 9744 foot-candles in the outdoor nursery. Plants grown in the shadehouse were approximately seven weeks from planting tubers when the photographs and the detailed description were taken. Plants grown in the outdoor nursery were approximately two months from planting tuber pieces when the photographs and the detailed description were taken.

DETAILED BOTANICAL DESCRIPTION OF THE NEW PLANT

Classification:
- *Family.*—Araceae.
- *Botanical.*—*Caladium×hortulanum.*
- *Common.*—*Caladium.*

Parentage: Selfing 'S79-206', (unpatented).

Propagation:
- *Type.*—By tubers and by tuber divisions.
- *Time to initiate roots, summer.*—Approximately seven to ten days at 32° C.
- *Time to initiate roots, winter.*—Approximately two to three weeks at 24° C.

Tuber description: Jumbo-sized (6.4 to 8.9 cm in diameter) tubers are multi-segmented, bearing six to nine dominant buds.
- *Height of No.1-sized tubers.*—Approximately 2.5 cm.
- *Diameter of No.1-sized tubers.*—Approximately 3.7 cm.
- *Texture.*—Thick, starchy; slightly brittle.
- *Color.*—Epidermis: brown (RHS 200C); Interior: yellow (RHS 10A).

Root description: Dense, thick and white fleshy roots.

Plant description:
- *Type.*—Herbaceous perennial.
- *Growth habit.*—Compact and mounding, dense foliage, suitable for 10.0 cm to 25.0 cm containers. Leaf petioles arising from tubers; petioles mostly semi-upright and curving outwardly with development.
- *Height, from soil level to top of leaf plane, shadehouse-grown plants.*—Approximately 27.0 cm to 34.0 cm.
- *Height, from soil level to top of inflorescences, shadehouse-grown plants.*—Approximately 35.0 cm.
- *Diameter or spread, shadehouse-grown plants.*—Approximately 59.0 cm×56.0 cm.
- *Height, from soil level to top of leaf plane, outdoor nursery-grown plants.*—Approximately 25.0 cm to 32.0 cm.
- *Height, from soil level to top of inflorescences, outdoor nursery-grown plants.*—Approximately 30.0 cm to 35.0 cm.
- *Diameter or spread, outdoor nursery-grown plants.*—Approximately 48.0 cm×39.0 cm.

Foliage description (shadehouse-grown and outdoor-grown):
- *Length, shadehouse-grown plants.*—Approximately 12.5 cm to 20.0 cm.
- *Width, shadehouse-grown plants (flattened).*—Approximately 8.5 cm to 13.0 cm.
- *Length, outdoor nursery-grown plants.*—Approximately 13.0 cm to 17.0 cm.
- *Width, outdoor nursery-grown plants (flattened).*—Approximately 9.5 cm to 12.0 cm.
- *Shape.*—Ovate.
- *Apex.*—Acuminate to acute.
- *Base.*—Cordate.
- *Margin.*—Entire; undulate.
- *Texture.*—Upper surface: Smooth, glabrous. Lower surface: Smooth, glabrous; glaucous.
- *Venation pattern.*—Pinnate.

Color, shadehouse-grown plants:
- *Developing and fully expanded leaves.*—Upper surface: Center: RHS 53A (Red). Border and margins: RHS 137A (Green). Basal notch: RHS 53C (Red). Venation: Midrib and primary veins: RHS 185A (Greyed-purple). Lower surface: Center: RHS 59A (Red-purple). Border and margins: RHS 138A (Green). Venation: Midrib and primary veins: RHS 182D (Greyed-red).

Color, outdoor nursery-grown plants:
- *Developing leaves.*—Upper surface: Center: RHS 185B (Greyed-purple). Border and margins: RHS 137A (Green). Venation: Midrib and primary veins: RHS 185A (Greyed-purple). Lower surface: Center: RHS 187D (Greyed-purple). Border and margins: RHS 138A (Green). Venation: Midrib and primary veins: RHS 182D (Greyed-red).
- *Fully expanded leaves.*—Upper Surface: Center: RHS 60B (Red-purple; very translucent). Border and margins: RHS 137A (Green). Venation: Midrib and primary veins: RHS 60A (Red-purple). Lower surface: Center: RHS 185B (Greyed-purple). Border and margins: RHS 138A (Green). Venation: Midrib RHS 182D (Greyed-red); primary vein RHS 196D (Green).

Petiole:
- *Aspect.*—Mostly erect, curving outwardly with development.
- *Length, shadehouse-grown plants.*—Approximately 18.0 to 30.0 cm.
- *Diameter, distal, shadehouse-grown plants.*—Approximately 3.2 mm.
- *Diameter, proximal, shadehouse-grown plants.*—Approximately 5.5 mm.
- *Length, outdoor nursery-grown plants.*—Approximately 21.5 cm to 27.0 cm.
- *Diameter, distal, outdoor nursery-grown plants.*—Approximately 3.4 mm.
- *Diameter, proximal, outdoor nursery-grown plants.*—Approximately 6.3 mm.
- *Strength.*—Strong; flexible.
- *Color, shadehouse-grown plants.*—RHS 158C and 158D (Yellow-white) and variably streaked with RHS 200C (Brown).
- *Color, proximal, outdoor nursery-grown plants.*—RHS 182D (Greyed-red), but lighter with blotches of RHS 200C (Brown).
- *Wing length, shadehouse-grown plants.*—Approximately 2.5 cm to 6.5 cm.
- *Wing diameter, shadehouse-grown plants.*—Approximately 4.0 mm to 6.0 mm.
- *Wing length, outdoor nursery-grown plants.*—Approximately 2.5 cm to 5.0 cm.

*Wing diameter, outdoor nursery-grown plants.*—Approximately 4.5 mm to 6.5 mm.

*Wing color, shadehouse-grown plants.*—RHS 158C and 158D (Yellow-white) with some streaks of RHS 200C (Brown).

*Wing color, outdoor nursery-grown plants.*—RHS 182D (Greyed-red), but lighter and with blotches of RHS 147A (Green).

Inflorescence description: Inflorescences have not been observed.

Seed and fruit: Seed and fruit development has not been observed.

Disease/pest resistance:

*Bacterial blight.*—Resistant.

*Xanthomonas leaf spot.*—Resistant.

Temperature tolerance: Tolerant to temperatures ranging from approximately 7° C. to approximately 40° C.

COMPARISON WITH PARENTAL VARIETY

'UF44-4' differs from its parent, *caladium* selection 'S79-206', by having approximately two times more leaves. Additionally, leaves of 'UF44-4' have a bright red center and green margins, whereas the leaves of *caladium* selection 'S79-206' have a light pink center and green margins.

COMPARISON WITH KNOWN CULTIVARS

'UF 44-4' can also be compared to plants of the cultivar 'Florida Sweetheart', disclosed in U.S. Plant Pat. No. 8,526. In side-by-side comparisons conducted in Wimauma, Fla., 'UF 44-4' primarily differed from plants of 'Florida Sweetheart' in leaf coloration and number of leaves. Leaves of 'Florida Sweetheart' were light pink in color in the center with dark green margins and pink-colored venation, whereas leaves of 'UF 44-4' have a bright red center. Additionally, the number of leaves on 'Florida Sweetheart' plants was approximately half the number of leaves of 'UF 44-4' plants.

'UF 44-4' was evaluated for tuber production and plant performance in Wimauma, Fla. in 2005 and 2006. The soil was an EauGallie fine sand with approximately 1% organic matter and a pH of 6.2. Plants were grown in a plastic mulched raised bed system maintaining a constant water table with seep irrigation. In 2005, ground beds were fumigated on February 25 (6 weeks before planting) with a mixture of 67% methyl bromide and 33% chloropicrin (by volume) at the rate of 392 kg×ha$^{-1}$. In 2006, the beds were fumigated on March 10, 10 days before planting, with the same fumigant mixture but at the half rate, 196 kg×ha$^{-1}$. The beds were 91 cm wide and 20 cm high with 2.54 cm *caladium* seed pieces (tuber pieces) planted 15 cm apart in 3 rows. Osmocote™ 18N-2.6P-10K 8-9 month controlled release fertilizer was applied to the bed surface when shoot tips were emerging from the soil with N at 336 kg×ha$^{-1}$.

Field plots were organized in a randomized complete block design consisting of three replications. For tuber production, each plot was 1.2 m$^2$ and contained 30 propagules. New tubers were harvested in November 2005 and December 2006, respectively. Tubers were dried in the greenhouse for approximately 4 weeks and then graded by their maximum diameter; No. 2 (2.5 cm to 3.8 cm), No. 1 (3.8 cm to 6.4 cm), Jumbo (6.4 cm to 8.9 cm), Mammoth (8.9 cm to 11.4 cm), and Super Mammoth (>11.4 cm). Production index, an indicator of economic value of the harvested tubers, was calculated for each plot, as follows: N (No. 2)+2N (No. 1)+4N (Jumbo)+6N (Mammoth)+8N (Super Mammoth); where N=number of tubers in each grade from each field plot. An analysis of variance was conducted to compare the performance of 'UF 44-4' to that of 'Florida Red Ruffles' (U.S. Plant Pat. No. 13,136), the most popular red lance leaf cultivar, and 'Florida Sweetheart', the most popular lance leaf cultivars in all colors. 'Red Frill' (unpatented), another commercial red lance leaf cultivar, was also included as a check in the trials in 2005 and 2006.

Table 1 shows the weight, production index, marketable number, and grade distribution of *caladium* tubers produced in 2005 and 2006 from 30 2.54 cm tuber propagules planted in 1.2 m$^2$ plot. Values presented are means of three replications in each year.

TABLE 1

| Cultivar | Tuber | | |
|---|---|---|---|
| | Weight (kg) | Production index | Marketable (no.) |
| | Year 2005 | | |
| Year 2005'UF 44-4' | 3.7 | 166.8 | 64.4 |
| 'Florida Red Ruffles' | 3.0 | 129.7 | 40.7 |
| 'Florida Sweetheart' | 3.3 | 144.3 | 46.7 |
| LSD ($\alpha$ = 0.05) | 0.4 | 11.3 | 7.1 |
| | Year 2006 | | |
| 'UF 44-4' | 3.3 | 118.6 | 49.7 |
| 'Florida Red Ruffles' | 2.3 | 87.9 | 43.8 |
| 'Florida Sweetheart' | 2.8 | 111.0 | 48.6 |
| 'Red Frill' | 1.2 | 67.7 | 38.8 |
| LSD ($\alpha$ = 0.05) | 1.1 | 31.0 | NS |

| Cultivar | Tuber distribution (%) | | | | |
|---|---|---|---|---|---|
| | Super mammoth | Mammoth | Jumbo | No. 1 | No. 2 |
| | Year 2005 | | | | |
| 'UF 44-4' | 0 | 7.0 | 28.1 | 39.7 | 25.1 |
| 'Florida Red Ruffles' | 0.8 | 15.6 | 35.2 | 33.1 | 15.2 |
| 'Florida Sweetheart' | 2.8 | 17.9 | 24.7 | 27.1 | 27.5 |
| LSD ($\alpha$ = 0.05) | NS | NS | NS | NS | NS |
| | Year 2006 | | | | |
| 'UF 44-4' | 2.5 | 7.1 | 17.5 | 42.8 | 30.0 |
| 'Florida Red Ruffles' | 0 | 6.5 | 19.7 | 30.1 | 42.7 |
| 'Florida Sweetheart' | 0.9 | 3.1 | 20.7 | 49.1 | 27.2 |
| 'Red Frill' | 0 | 0 | 1.4 | 66.8 | 31.9 |
| LSD ($\alpha$ = 0.05) | NS | NS | 7.2 | 27.4 | NS |

NS: not significantly different at $P < 0.05$.

As shown in Table 1, in 2005, 'UF 44-4's tuber weight was 3.7 kg, its production index was 166.8, and its number of marketable tubers was 64.4 per plot. Its tuber weight was 23% greater than 'Florida Red Ruffles' (3.0 kg) and 12% greater than 'Florida Sweetheart's (3.3 kg). The production index for 'UF 44-4' was 29% and 15% higher than that of 'Florida Red Ruffles' (129.7) and 'Florida Sweetheart' (144.3), respectively. 'UF 44-4' produced 58% and 38% more tubers than 'Florida Red Ruffles' and 'Florida Sweetheart', respectively.

Also shown in Table 1, in 2006, 'UF 44-4' tuber weight (3.3 kg) was 43% and 18% higher than 'Florida Red Ruffles' (2.3 kg) and 'Florida Sweetheart' (2.8 kg), but the difference was not statistically significant. In production index and number of marketable tubers, 'UF 44-4' is comparable to 'Florida Red Ruffles' and 'Florida Sweetheart'. 'UF 44-4's tuber weight was approximately 1.8 fold higher, and production index was 75% greater than 'Red Frill'.

In tuber grade distribution, the majority (60% or more) of tubers of 'UF 44-4' were in the categories of No. 1, Jumbo, or Mammoth, which was similar to the size distribution of 'Florida Red Ruffles' and 'Florida Sweetheart'. 'UF 44-4' produced more large tubers (Mammoth and Jumbo) than 'Red Frill', which had the majority (>95%) of tubers in the No. 1 and No. 2 categories.

Table 2 shows a comparison of the plant height, number of leaves, leaf length and leaf width of 'UF 44-4' and three commercial cultivars approximately 4 months from planting 2.54-cm tuber propagules in ground beds in full sun in 2005 and 2006. Values presented are means of three replications with three plants measured per plot per year.

TABLE 2

| Cultivar | Plant height (cm) | Leaves (no.) | Leaf length (cm) | Leaf width (cm) |
|---|---|---|---|---|
| 'UF 44-4' | 30.1 | 42.7 | 19.2 | 12.7 |
| 'Florida Red Ruffles' | 21.9 | 26.3 | 18.2 | 10.7 |
| 'Florida Sweetheart' | 24.2 | 21.5 | 20.0 | 13.3 |
| 'Red Frill' | 14.3 | 20.9 | 14.8 | 7.9 |
| LSD ($\alpha = 0.05$) | 4.7 | 10.9 | 3.0 | 1.5 |

As shown in Table 2, plants of 'UF 44-4' were 6 to 8 cm taller than those of 'Florida Red Ruffles' and 'Florida Sweetheart'. Leaves of 'UF 44-4' were similar to those of 'Florida Sweetheart', but approximately 2 cm wider than those of 'Florida Red Ruffles'. The most significant difference among the entries was in the leaf number produced per plant: 42.7 by 'UF 44-4' vs. 20.9 to 26.3 by 'Florida Red Ruffles', 'Florida Sweetheart' or 'Red Frill'.

Table 3 shows plant performance and sun burn tolerance of 'UF 44-4' and three commercial cultivars (checks) when planted in ground beds in full sun in 2005, 2006 and 2007. Values presented are means of three replications in each year.

Landscape performance of 'UF 44-4' was evaluated on the same plots used for evaluating tuber production. A scale of 1 to 5 was used with 1 being very poor (few leaves and lack of vigor), and 5 being excellent (full plants, numerous leaves, and bright color display). Leaf sun burn tolerance also was evaluated on a scale of 1 to 5, with 1 being very susceptible to sun burns (leaves having numerous sun-damaged areas or holes) and 5 being resistant to sun burns (no visible sun-damaged areas). A total of eight evaluations were conducted for plant performance and sun burn tolerance over three growing seasons in June, July and August 2005, August and September 2006, and July, August and September 2007. Approximately 4 months after planting, plant height, number of leaves and leaf size were measured on three randomly chosen plants in each plot.

TABLE 3

| | Performance rating | | | | | | | |
|---|---|---|---|---|---|---|---|---|
| | 2005 | | | 2006 | | 2007 | | |
| Cultivar | June | July | August | August | September | July | August | September |
| 'UF 44-4' | 3.4 | 4.7 | 4.8 | 3.5 | 4.0 | 4.0 | 4.0 | 4.0 |
| 'Florida Red Ruffles' | 2.8 | 4.1 | 4.3 | 2.0 | 3.0 | 3.8 | 3.1 | 2.9 |
| 'Florida Sweetheart' | 2.6 | 3.8 | 4.1 | 3.3 | 4.0 | 3.3 | 3.1 | 2.8 |
| 'Red Frill' | —[z] | — | — | 2.5 | 2.5 | 4.2 | 2.8 | 2.0 |
| LSD ($\alpha = 0.05$) | 0.7 | 0.8 | 0.4 | 1.3 | 0.5 | 0.8 | 0.6 | 1.1 |

TABLE 3-continued

| | Sun tolerance rating | | | | | | | |
|---|---|---|---|---|---|---|---|---|
| | 2005 | | | 2006 | | 2007 | | |
| Cultivar | June | July | August | August | September | July | August | September |
| 'UF 44-4' | 3.5 | 4.7 | 4.5 | 3.8 | 4.3 | 3.7 | 4.6 | 4.0 |
| 'Florida Red Ruffles' | 3.6 | 4.4 | 4.3 | 4.0 | 4.7 | 3.5 | 4.3 | 4.0 |
| 'Florida Sweetheart' | 3.0 | 4.1 | 4.2 | 4.0 | 4.6 | 3.5 | 4.3 | 3.8 |
| 'Red Frill' | — | — | — | 3.8 | 4.2 | 3.8 | 3.4 | 2.3 |
| LSD ($\alpha = 0.05$) | NS[y] | NS | NS | NS | 0.3 | NS | 0.7 | 0.3 |

[z]This cultivar was not included in the trial in 2005.
[y]Not significantly different at $P \leq 0.05$.

As shown in Table 3, with a superb number of leaves, 'UF 44-4' produced full plants with bright color display and received the highest ratings for plant performance: 3.4-3.5 in June 2005 and August 2006, 4.0 in September 2006 and July, August and September 2007, and 4.7-4.8 in July and August 2005. 'UF 44-4's plant performance rating was significantly higher than that of 'Florida Red Ruffles' in four out of eight evaluations and significantly higher than that of 'Florida Sweetheart' in six out of eight evaluations.

The suitability of 'UF 44-4' for potted plant production was evaluated by forcing tubers in 11.4 cm containers. No. 1 tubers were planted either intact or de-eyed in a peat/vermiculite mix on 26 Mar. 2007. The study was conducted in a greenhouse with 45% light exclusion during the summer in Wimauma, Fla. Average daily temperatures ranged from a low of 16° C. night to 29° C. day during the experiment. Potted plants were arranged on metal benches in the greenhouse in a randomized complete block design with 10 replications. Plant height, number of leaves, and foliar characteristics were recorded 8 weeks after planting.

Table 4 shows a comparison of number of days to sprout, plant height, leaf number, leaf length, leaf width, and quality rating for *caladium* cultivars grown from No. 1 tubers in 11.4 cm containers in a 45% shaded glasshouse in Wimauma, Fla. in 2007. Values represent the means of 10 plants produced from intact or de-eyed No. 1 (>3.8 and <6.4 cm in diameter) tubers planted individually per container.

TABLE 4

| | Days to sprout [z] | | Plant height (cm) | |
|---|---|---|---|---|
| Cultivar | Intact | De-eye | Intact | De-eye |
| UF 44-4 | 38.6 | 38.0 | 16.3 | 14.4 |
| Florida Red Ruffles | 36.8 | 39.6 | 16.1 | 16.6 |
| Florida Sweetheart | 42.3 | 40.0 | 17.3 | 16.2 |
| Red Frill | 30.9 | 31.5 | 10.8 | 11.3 |
| LSD ($\alpha = 0.05$) | 4.5 | 4.4 | 3.1 | 2.4 |

| | Leaves (no.) | | Leaf length (cm) | |
|---|---|---|---|---|
| Cultivar | Intact | De-eye | Intact | De-eye |
| UF 44-4 | 10.0 | 17.2 | 16.2 | 16.4 |
| Florida Red Ruffles | 9.4 | 13.3 | 17.7 | 17.5 |

TABLE 4-continued

| | | | | |
|---|---|---|---|---|
| Florida Sweetheart | 10.9 | 14.8 | 17.5 | 16.4 |
| Red Frill | 10.8 | 16.7 | 15.1 | 14.1 |
| LSD ($\alpha = 0.05$) | NS | NS[y] | NS | 1.8 |

| | Leaf width (cm) | | Quality rating | |
|---|---|---|---|---|
| Cultivar | Intact | De-eye | Intact | De-eye |
| UF 44-4 | 12.1 | 10.3 | 4.1 | 4.5 |
| Florida Red Ruffles | 12.5 | 12.3 | 3.5 | 4.1 |
| Florida Sweetheart | 10.9 | 10.6 | 3.2 | 4.0 |
| Red Frill | 10.7 | 9.9 | 2.8 | 3.9 |
| LSD ($\alpha = 0.05$) | NS | 1.9 | 0.5 | 0.4 |

[z] Number of days from planting to the first unfurled leaf .
[y] Not significantly different at $P \leq 0.05$.

As shown in Table 4, 'UF 44-4' produced high quality potted plants regardless of tuber treatments (intact or de-eyed). When tubers were planted intact, 'UF 44-4' sprouted approximately 39 days after planting, which was similar to the sprouting time of 'Florida Red Ruffles' and 'Florida Sweetheart', but approximately 8 days later than 'Red Frill'. Tuber de-eyeing did not cause any change in sprouting time in 'UF 44-4'. Intact plants of 'UF 44-4', 'Florida Red Ruffles' and 'Florida Sweetheart' were similar in plant height (16.3 cm, 16.1 cm, and 17.3 cm), numbers of leaves (10, 9.4, and 10.9), leaf lengths (16.2 cm, 17.7 cm, and 17.5 cm) and leaf widths (12.1 cm, 12.5 cm, and 10.9 cm). When plants were de-eyed, 'UF 44-4', 'Florida Red Ruffles' and 'Florida Sweetheart' were similar in leaf length (16.4 cm, 17.5 cm, and 16.4 cm) and leaf width (10.3 cm, 12.3 cm, and 10.6 cm), but 'UF 44-4' had 3-4 more leaves and was approximately 2 cm shorter in plant height than 'Florida Red Ruffles' and 'Florida Sweetheart'. With multiple bright red leaves, pot-grown 'UF 44-4' plants received the highest quality ratings (4.1 and 4.5) compared to the three check cultivars (2.8 to 4.1). Quality pot plants were produced without de-eyeing, but de-eyeing appeared to improve plant quality rating (from 4.1 to 4.5).

We claim:

1. A new and distinct *caladium* plant named 'UF 44-4' as illustrated and described herein.

* * * * *